United States Patent [19]
von Bittera et al.

[11] Patent Number: 4,582,717
[45] Date of Patent: Apr. 15, 1986

[54] PROCESS FOR PRODUCTION OF VAGINAL TAMPONS CONTAINING PHARMACEUTICAL ACTIVE COMPOUND

[75] Inventors: Miklos von Bittera, Leverkusen; Karl H. Büchel, Burscheid; Manfred Plempel; Erik Regel, both of Wuppertal, all of Fed. Rep. of Germany

[73] Assignee: Bayer Aktiengesellschaft, Leverkusen, Fed. Rep. of Germany

[21] Appl. No.: 634,941

[22] Filed: Jul. 27, 1984

Related U.S. Application Data
[62] Division of Ser. No. 460,083, Jan. 21, 1983, abandoned.

[30] Foreign Application Priority Data
Feb. 6, 1982 [DE] Fed. Rep. of Germany ....... 3204124

[51] Int. Cl.$^4$ .................. A01N 1/02; A61F 13/16; A61F 13/18; A61F 13/20
[52] U.S. Cl. ................................ 427/2; 424/19; 424/28; 604/358; 604/904
[58] Field of Search ............ 424/19, 28; 604/904, 604/358; 427/2

[56] References Cited

U.S. PATENT DOCUMENTS

| | | | |
|---|---|---|---|
| 3,393,678 | 7/1968 | Pacini | 424/28 X |
| 3,481,335 | 12/1969 | Beutlich | 424/28 X |
| 3,691,271 | 9/1972 | Charle et al. | 424/28 |
| 3,724,465 | 4/1973 | Duchane | 604/904 X |
| 3,995,636 | 12/1976 | Murray et al. | 604/904 X |
| 4,340,055 | 7/1982 | Sneider | 604/904 X |

OTHER PUBLICATIONS

Current Therapeutic Research, vol. 23, No. 6, Jun., 1978 (5 pages) Miconazole In Vaginal Tampons A New Treatment of Vaginal Candidiasis.

*Primary Examiner*—Michael R. Lusignan
*Attorney, Agent, or Firm*—Sprung, Horn, Kramer & Woods

[57] ABSTRACT

The invention relates to a process for production of tampons containing novel formulations of antimycotic azole derivatives which provide a higher release of active compounds and make short-term therapy possible. The tampon formulations of the invention contain active antimycotic azole derivatives in impregnated form, only melting at body temperature, or dissolved form, such as, for example, in suppository bases or their combinations with emulsifiers and/or spreading agents and/or solubilisers.

1 Claim, No Drawings

PROCESS FOR PRODUCTION OF VAGINAL TAMPONS CONTAINING PHARMACEUTICAL ACTIVE COMPOUND

This is a division of application Ser. No. 460,083 filed Jan. 21, 1983 now abandoned.

The present invention relates to novel formulations of the known antimycotic azole derivatives, which exhibit a higher release of the active compounds and thereby make short-term therapy possible.

Formulations of antimycotic azole derivatives, which form tampons, for the treatment of vaginal infections with fungi have already been disclosed [Current Therapeutic Research, Vol. 23, No.6, June 1978, 661–665]. With these formulations, 14 to 3 days therapy time are necessary to complete vaginal clean-up. This is attributable, inter alia, to the fact that the active compound contained in the known tampon formulations is only partially soluble in aqueous media. However, it is desirable to have tampons available with which briefer therapy is possible.

In order to achieve a shortening of the duration of therapy for vaginal mycoses, particularly for eliminating the organisms, and in order to achieve a reliable mycological clean-up, a higher release of the active compounds in the aqueous medium is required. The known formulations are only suitable to limited extent for this purpose, since only a small proportion of the active compound available dissolves in the volume of liquid at the site of infection. The tampons are coated with a carrier material which consists of a base which only melts above body temperature and in which the active compound is present in the form of coarse crystals and is unchanged at body temperature.

In tampons coated in this manner, the active compound is slowly and gradually dissolved out and there exists the danger that the released active compound is absorbed again in the swelling tampons. For this reason, in vitro release results exhibit an effectiveness which fluctuates very widely and differs locally on the tampon. If it is now intended to achieve a shortening of the duration of therapy, for example to one day with administration three times, by or without further increase in the concentration of active compound, care must be taken that the bioavailability of the active compound is optimal.

It has not been found that those tampon formulations of antimycotic azole derivatives which contain the active compound in an impregnated form, only melting at body temperature, or dissolved form, such as, for example, in suppository bases or their combinations with emulsifiers and/or spreading agents and/or solubilisers, release the active compound to a greater extent and thereby make possible a shortening of the duration of therapy to 1 day. This effect of the higher release of active compound can extend up to a power of ten.

Active compounds which can be formulated in this manner are all derivatives having antimycotic activity, in particular imidazole and triazole derivatives. They are present in the tampons according to the invention in amounts of 50–300 mg, preferably of 100–200 mg.

The compounds of the formulae below may be mentioned as examples:

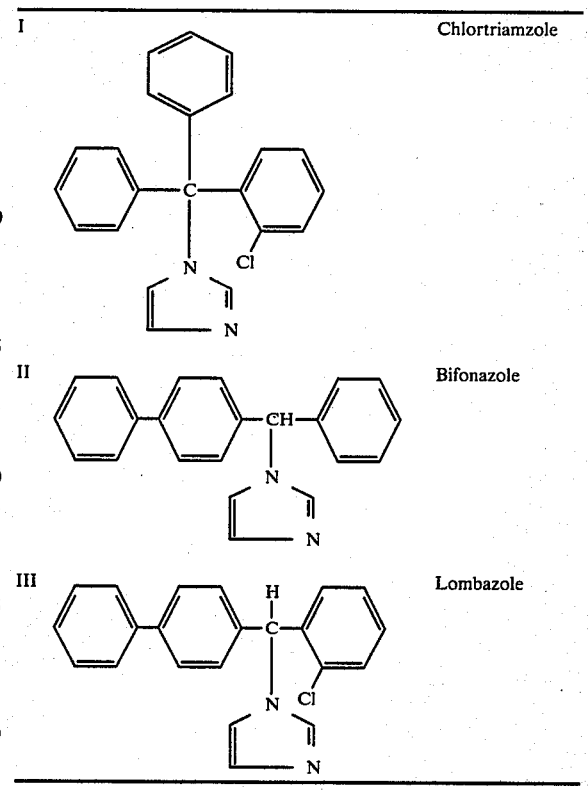

Numerous other azole derivatives having antimycotic activity are disclosed in DE-OS (German Published Specification) No. 2,430,039. They can equally serve as active compounds in the agents according to the invention.

The carrier material for impregnation must comply with the following requirements:

Sufficient consistency at room temperature, homogeneity, sufficient ability to dissolve the active compound, sufficient ability to release it, suitable melting characteristics and uniform in vitro effectiveness.

The following possible combinations are suitable for impregnation:
Suppository bases with emulsifier.
Suppository bases with emulsifier+lactic acid.
Suppository bases with solubilisers.
Suppository bases with spreading agents.
Suppository bases with spreading agent and solubiliser.
Solid spreading agents melting at body temperature.
Solid spreading agents melting at body temperature with spreading oils.
Solid spreading agents melting at body temperature with spreading oils and solubiliser.
Solid solvents melting at room temperature, for example ethylene carbonate.
Solid solvents melting at body temperature with additional solubilisers.

The following suppository bases are suitable as carrier material for the agents according to the invention:

Mixtures of triglycerides of natural saturated fatty acids of chain length $C_{10}$–$C_{18}$, triglycerides of mixtures of natural saturated plant fatty acids of chain length $C_{10}$–$C_{18}$, glycerol esters of mixtures of plant saturated fatty acids, lauric acid predominating. Suppository bases having a very low hydroxyl number. Bases free of hydroxyl groups. The abovementioned bases with emulsifier, for example non-ionic emulsifiers, such as saturated $C_{16}$–$C_{18}$ fatty alcohol etherified with 25 mol of ethylene oxide etc.

Mixtures of mono-, di- and triglycerides of saturated natural fatty acids of chain length $C_{12}$–$C_{18}$, with or without emulsifiers.

Mixtures of mono-, di- and triglycerides, fatty alcohols, wax esters, etc.

For the agents according to the invention, the following compounds are, for example, suitable as solid spreading agents melting at body temperature: myristyl lactate, cetyl lactate, myristyl myristate and similar compounds.

Spreading agents are understood to include oily fluids which distribute particularly well on the skin [R. Keymer, Pharm. Ind. 32, 577–581 (1970)].

For the agents according to the invention, the following compounds are particularly suitable as spreading agents or oils:

Silicone oils of various viscosity.

Fatty acid esters, such as ethyl stearate, di-n-butyl adipate, hexyl laurate, dipropylene glycol pelargonate, esters of a branched fatty acid of moderate chain length with saturated fatty alcohols $C_{16}$–$C_{18}$, isopropyl myristate, isopropyl palmitate, caprylic/capric acid esters of separated fatty alcohols of chain length $C_{12}$–$C_{18}$, isopropyl stearate, oleyl oleate, decyl oleate, ethyl oleate, wax-like fatty acid esters, such as artificial duck preen gland fat, dibutyl phthalate, diisopropyl adipate, ester mixtures related to the latter and the like.

Triglycerides, such as caprylic/capric acid triglyceride, mixtures of triglycerides with plant fatty acids of chain length $C_8$–$C_{12}$ or other specially selected natural fatty acids, partial glyceride mixtures of saturated or unsaturated fatty acids, possibly also containing hydroxyl groups, monoglycerides of $C_8$/$C_{10}$ fatty acids and the like.

Fatty alcohols, such as isotridecyl alcohol, cetylstearyl alcohol and oleyl alcohol.

Fatty acids, such as, for example, oleic acid.

The following are particularly well suited spreading oils: isopropyl myristate, isopropyl palmitate, caprylic/-capric acid esters of saturated fatty alcohols of chain length $C_{12}$–$C_{18}$, wax-like fatty acid esters such as artificial duck preen gland fat, silicone oils and isopropyl myristate/isopropyl stearate/isopropyl palmitate mixture.

Glycerol, high viscosity paraffin and low viscosity paraffin.

For the agents according to the invention, the following agents are suitable as emulsifiers:

Colloidal-disperse mixture of cetylstearyl alcohol and sodium cetylstearyl sulphate, polyethylene stearate, cetylstearyl alcohol with about 12 mol of ethylene oxide, cetylstearyl alcohol with about 30 mol of ethylene oxide, fatty alcohol $C_{16}$–$C_{18}$ etherified with 25 mol of ethylene oxide, sorbitan and glycerol fatty acid esters, ethoxylated castor oil and cetylstearyl alcohol with addition of non-ionic emulsifier.

The following other auxiliaries and/or formulation base auxiliaries can be used in manufacturing the agents according to the invention:

Surfactant (contains emulsifiers and wetting agent), for example 1. anion-active, such as Na lauryl sulphate, fatty alcohol ether sulphates, mono/dialkylpolyglycol ether orthophosphates-monoethanolamine salt;
2. cation-active, such as cetyltrimethylammonium chloride;
3. ampholytic, such as di-Na N-lauryl-β-ininodipropionate or lecithin;
4. non-ionic, for example polyoxyethylated castor oil, polyoxyethylated sorbitan monooleate, sorbitan monostearate or cetyl alcohol. Glycerol monostearate, polyoxyethylene stearate, alkylphenol polyglycol ethers and similar compounds.

For the agents according to the invention, ethylene carbonate and polyethylene glycols having moderate molecular weights are suitable as solid solvents only melting at body temperature.

The following compounds can be employed as solubilisers:

2-Octyldodecanol, benzyl alcohol, ethyl lactate, propylene glycol, di- and tripropylene glycol and the like.

All qualities of commercially available, specially treated, compressed cotton can be used as the tampon.

The tampons according to the invention are manufactured in the following manner:

(a) Coating

The basic material consisting of active compound and formulating auxiliaries, melted and cooled down to 40° C., was weighed in portions of 2.0 g into 3 cm high glass vessels having a diameter of 1.5 cm. The pre-cooled tampons were pressed into the material so that they were surrounded at the level of the glass rim by the solidifying material.

The glass vessels with the tampons were wrapped in aluminium foil for protection from moisture and placed in a refrigerator to complete solidification. The coated tampons could subsequently be easily removed from the glass vessels.

(b) Impregnation

The basic material consisting of active compound and formulating auxiliaries, melted and cooled down to 40° C., was injected, using a pre-warmed 2 ml injection syringe, the capacity of which had previously been calibrated to 2.0 g by injection into tared tampons, from the point into pre-warmed tampons which were still wrapped in protective foil.

In order to prevent the basic material solidifying too rapidly, which would make uniform impregnation difficult, the impregnated tampons were placed with the point at the bottom in pre-warmed vessels and thus cooled down slowly.

The process described according to (b) makes possible on the large-scale a rapid, uncomplicated and more exact manufacture. The tampons impregnated by this process, compared to tampons coated according to (a), show a more uniform vitro release of active compound and thus also exhibit a better therapeutic effectiveness.

The impregnation material must comply with the following requirements: sufficient consistency up to 32° C., homogeneity, sufficient ability to dissolve the active compound, sufficient ability to release it, suitable melting characteristics and good in vitro effectiveness.

PREPARATION EXAMPLES

Example 1

| Chlortrimazole (coated) | 200 mg/tampon |
|---|---|
| Mixture of mono-, di- and triglycerides of saturated natural fatty acids of chain length $C_{12}-C_{18}$ | 1,450 mg |
| Cetylstearyl alcohol with non-ionic emulsifier | 150 mg |
| Lactic acid | 200 mg |

Example 2

| Clotrimazole (coated) | 200 mg/tampon |
|---|---|
| Mixture of mono-, di- and triglycerides of saturated natural fatty acids of chain length $C_{12}-C_{18}$ | 1,600 mg |
| Benzyl alcohol | 200 mg |

Example 3

| Clotrimazole (coated) | 200 mg/tampon |
|---|---|
| Mixture of mono-, di- and triglycerides of saturated fatty acids of chain length $C_{12}-C_{18}$ | 1,650 mg |
| Benzyl alcohol | 150 mg |

The following Examples 4-43 deal with impregnated formulations.

Example 4

| Clotrimazole | 200 mg/tampon |
|---|---|
| Triglyceride mixture of natural saturated fatty acids of chain length $C_{10}-C_{18}$ | 800 mg |
| Benzyl alcohol | 200 mg |
| Myristyl myristate | 800 mg |

Example 5

| Clotrimazole | 200 mg/tampon |
|---|---|
| Mixture of mono-, di- and triglycerides of saturated fatty acids of chain length $C_{12}-C_{18}$ | 800 mg |
| Ethyl lactate | 200 mg |
| Benzyl alcohol | 100 mg |
| Myristyl myristate | 700 mg |

Example 6

| Clotrimazole | 200 mg/tampon |
|---|---|
| Benzyl alcohol | 80 mg |
| Myristyl lactate | 860 mg |
| Myristyl myristate | 860 mg |

Example 7

| Clotrimazole | 200 mg/tampon |
|---|---|
| Mixture of mono-, di- and triglycerides of saturated fatty acids of chain length $C_{12}-C_{18}$ | 800 mg |
| Ethyl lactate | 200 mg |
| Myristyl myristate | 800 mg |

Example 8

| Clotrimazole | 200 mg/tampon |
|---|---|
| Mixture of mono-, di- and triglycerides of saturated fatty acids of chain length $C_{12}-C_{18}$ | 800 mg |
| Ethyl lactate | 200 mg |
| Myristyl lactate | 800 mg |

Example 9

| Clotrimazole | 200 mg/tampon |
|---|---|
| Triglyceride mixture of natural saturated fatty acids of chain length $C_{10}-C_{18}$ | 800 mg |
| Ethyl lactate | 200 mg |
| Benzyl alcohol | 100 mg |
| Myristyl myristate | 700 mg |

Example 10

| Clotrimazole | 200 mg/tampon |
|---|---|
| Mixture of mono-, di- and triglycerides of saturated fatty acids of chain length $C_{12}-C_{18}$ | 1,000 mg |
| Benzyl alcohol | 100 mg |
| Isopropyl myristate | 100 mg |
| Myristate lactate | 400 mg |

Example 11

| Clotrimazole | 200 mg/tampon |
|---|---|
| Mixture of mono-, di- and triglycerides of saturated fatty acids of chain length $C_{12}-C_{18}$ | 600 mg |
| Benzyl alcohol | 100 mg |
| Hexyl laurate | 300 mg |
| Myristyl myristate | 800 mg |

Example 12

| Clotrimazole | 200 mg/tampon |
|---|---|
| Mixture of mono-, di- and triglycerides of saturated fatty acids of chain length $C_{12}-C_{18}$ | 1,600 mg |
| Ethyl lactate | 200 mg |

Example 13

| Clotrimazole | 200 mg/tampon |
|---|---|
| Benzyl alcohol | 100 mg |
| Hexyl laurate | 300 mg |
| Myristyl myristate | 1,400 mg |

Example 14

| Clotrimazole | 200 mg/tampon |
|---|---|
| Ethylene carbonate | 1,800 mg |

Example 15

| Clotrimazole | 200 mg/tampon |
|---|---|
| Benzyl alcohol | 100 mg |
| Ethylene carbonate | 1,700 mg |

Example 16

| Clotrimazole | 200 mg/tampon |
|---|---|
| Ethylene carbonate | 1,700 mg |
| 2-Octyldodecanol | 100 mg |

Example 17

| Clotrimazole | 100 mg/tampon |
|---|---|
| Mixture of mono-, di- and triglycerides of chain length $C_{12}$–$C_{18}$ | 844.6 mg |
| Ethyl lactate | 211.0 mg |
| Benzyl alcohol | 105.4 mg |
| Myristyl myristate | 739.0 mg |

Example 18

| Clotrimazole | 100 mg/tampon |
|---|---|
| Triglyceride mixture of natural saturated fatty acids of chain length $C_{10}$–$C_{18}$ | 844.6 mg |
| Ethyl lactate | 211.0 mg |
| Benzyl alcohol | 105.4 mg |
| Myristyl myristate | 739.0 mg |

Example 19

| Clotrimazole | 100 mg/tampon |
|---|---|
| Mixture of mono-, di- and triglycerides of chain length $C_{12}$–$C_{18}$ | 1,055.2 mg |
| Ethyl lactate | 211.0 mg |
| Benzyl alcohol | 105.4 mg |
| Myristyl lactate | 423.0 mg |
| Isopropyl myristate | 105.4 mg |

Example 20

| Clotrimazole | 100 mg/tampon |
|---|---|
| Mixture of mono-, di- and triglycerides of saturated fatty acids of chain length $C_{12}$–$C_{18}$ | 633.4 mg |
| Ethyl lactate | 211.0 mg |
| Benzyl alcohol | 105.4 mg |
| Myristyl myristate | 633.4 mg |
| Hexyl laurate | 316.8 mg |

Example 21

| Clotrimazole | 100 mg/tampon |
|---|---|
| Benzyl alcohol | 105 mg |
| Ethylene carbonate | 1,795 mg |

Example 22

| Clotrimazole | 100 mg/tampon |
|---|---|
| Polyglycol with a molecular weight of 1,000 | 450 mg |
| Polyglycol with a molecular weight of 1,500 | 1,350 mg |
| Benzyl alcohol | 100 mg |

Example 23

| Clotrimazole | 100 mg/tampon |
|---|---|
| Mixture of mono-, di- and triglycerides of saturated fatty acids of chain length $C_{12}$–$C_{18}$ | 900 mg |
| Ethyl lactate | 200 mg |
| Benzyl alcohol | 100 mg |
| Myristyl myristate | 700 mg |

Example 24

| Clotrimazole | 100 mg/tampon |
|---|---|
| Triglyceride mixture of natural saturated fatty acids of chain length $C_{10}$–$C_{18}$ with addition of 2% of a non-ionic emulsifier | 800 mg |
| Ethyl lactate | 300 mg |
| Benzyl alcohol | 100 mg |
| Myristyl myristate | 700 mg |

Example 25

| Clotrimazole | 100 mg/tampon |
|---|---|
| Triglyceride mixture of natural saturated fatty acids of chain length $C_{10}$–$C_{18}$ | 800 mg |
| Ethyl lactate | 400 mg |
| Myristyl myristate | 700 mg |

Example 26

| Clotrimazole | 100 mg/tampon |
|---|---|
| Triglycerides of saturated fatty acids of chain length $C_{12}$–$C_{18}$ | 500 mg |
| Ethyl lactate | 100 mg |
| Isopropyl myristate | 200 mg |
| Myristyl lactate | 400 mg |
| Myristyl myristate | 500 mg |

Example 27

| Clotrimazole | 100 mg/tampon |
|---|---|
| Triglycerides of saturated fatty acids of chain length $C_{12}$–$C_{18}$ | 800 mg |

-continued

| | |
|---|---|
| Ethyl lactate | 400 mg |
| Benzyl alcohol | 100 mg |
| Isopropyl myristate | 300 mg |
| Myristyl lactate | 300 mg |

Example 28

| | |
|---|---|
| Clotrimazole | 100 mg/tampon |
| Triglycerides of saturated fatty acids of chain length $C_{12}$–$C_{18}$ | 900 mg |
| Ethyl lactate | 400 mg |
| Isopropyl myristate | 300 mg |
| Myristyl lactate | 300 mg |

Example 29

| | |
|---|---|
| Clotrimazole | 100 mg/tampon |
| Triglycerides of saturated fatty acids of chain length $C_{12}$–$C_{18}$ | 500 mg |
| Ethyl acetate | 200 mg |
| Benzyl alcohol | 100 mg |
| Hexyl laurate | 200 mg |
| Myristyl lactate | 400 mg |
| Myristyl myristate | 500 mg |

Example 30

| | |
|---|---|
| Clotrimazole | 100 mg/tampon |
| Triglycerides of saturated fatty acids of chain length $C_{12}$–$C_{18}$ | 900 mg |
| Ethyl lactate | 200 mg |
| Benzyl alcohol | 100 mg |
| Hexyl laurate | 300 mg |
| Myristyl lactate | 400 mg |

Example 31

| | |
|---|---|
| Clotrimazole | 100 mg/tampon |
| Triglycerides of saturated fatty acids of chain length $C_{12}$–$C_{18}$ | 900 mg |
| Ethyl lactate | 400 mg |
| Hexyl laurate | 300 mg |
| Myristyl lactate | 300 mg |

Example 32

| | |
|---|---|
| Clotrimazole | 100 mg/tampon |
| Triglycerides of saturated fatty acids of chain length $C_{12}$–$C_{18}$ | 650 mg |
| Ethyl lactate | 220 mg |
| Benzyl alcohol | 110 mg |
| Hexyl laurate | 320 mg |
| Myristyl myristate | 600 mg |

Example 33

| | |
|---|---|
| Clotrimazole | 100 mg/tampon |
| Triglycerides of saturated fatty acids of chain length $C_{12}$–$C_{18}$ | 800 mg |
| Triglyceride mixture of natural saturated fatty acids of chain length $C_{10}$–$C_{18}$ with addition of 2% of non-ionic emulsifier | 800 mg |
| Ethyl lactate | 300 mg |

Example 34

| | |
|---|---|
| Clotrimazole | 100 mg/tampon |
| Polyglycol molecular weight 1,000 | 350 mg |
| Polyglycol molecular weight 1,500 | 1,050 mg |
| Ethyl lactate | 500 mg |

Example 35

| | |
|---|---|
| Clotrimazole | 100 mg/tampon |
| Polyglycol molecular weight 1,000 | 400 mg |
| Polyglycol molecular weight 1,500 | 1,100 mg |
| Ethyl lactate | 200 mg |
| Benzyl alcohol | 100 mg |

Example 36

| | |
|---|---|
| Clotrimazole | 100 mg/tampon |
| Polyglycol molecular weight 1,000 | 360 mg |
| Polyglycol molecular weight 1,500 | 1,140 mg |
| Solubiliser of fatty acid glycerol polyglycol esters and fatty acid polyglycol esters obtained by reaction of hydrogenated castor oil with E.O., and polyethylene glycols and glycerol ethoxylate | 400 mg |

Example 37

| | |
|---|---|
| Clotrimazole | 100 mg/tampon |
| Ethyl lactate | 300 mg |
| Polyglycol molecular weight 1,000 | 400 mg |
| Polyglycol molecular weight 1,500 | 1,000 mg |
| Solubiliser as in Example 36 | 200 mg |

Example 38

| | |
|---|---|
| Bifonazole | 100 mg/tampon |
| Mixture of of mono-, di- and triglycerides of saturated fatty acids of chain length $C_{12}$–$C_{18}$ | 900 mg |
| Ethyl lactate | 400 mg |
| Hexyl laurate | 300 mg |
| Myristyl lactate | 300 mg |

Example 39

| | |
|---|---|
| Bifonazole | 100 mg/tampon |
| Triglyceride mixture of natural saturated fatty acids of chain length $C_{10}$-$C_{18}$ with the addition of 2% of non-ionic emulsifier | 800 mg |
| Ethyl lactate | 400 mg |
| Benzyl alcohol | 100 mg |
| Myristyl myristate | 700 mg |

Example 40

| | |
|---|---|
| Bifonazole | 100 mg/tampon |
| Polyglycol molecular weight 1,000 | 400 mg |
| Polyglycol molecular weight 1,500 | 1,000 mg |
| Ethyl lactate | 200 mg |
| Benzyl alcohol | 100 mg |

Example 41

| | |
|---|---|
| Lombazole | 100 mg/tampon |
| Mixture of mono-, di- and triglycerides of saturated fatty acids of chain length $C_{12}$-$C_{18}$ | 900 mg |
| Ethyl lactate | 400 mg |
| Hexyl laurate | 300 mg |
| Myristyl lactate | 300 mg |

Example 42

| | |
|---|---|
| Lombazole | 100 mg/tampon |
| Triglyceride mixture of natural saturated fatty acids of chain length $C_{10}$-$C_{18}$ with the addition of 2% of non-ionic emulsifier | 800 mg |
| Ethyl lactate | 300 mg |
| Benzyl alcohol | 100 mg |
| Myristyl myristate | 700 mg |

Example 43

| | |
|---|---|
| Lombazole | 100 mg/tampon |
| Polyglycol molecular weight 1,000 | 400 mg |
| Polyglycol molecular weight 1,500 | 1,100 mg |
| Ethyl lactate | 200 mg |
| Benzyl alcohol | 100 mg |

Testing the effectiveness of the tampons according to the invention was carried out by sensitivity measurement in the agar diffusion test for Candida albicans and Torulopsis glabrata in accordance with the following method:

In order to measure the release of active compound, 2 each of the different vaginal tampons, impregnated in each case with 100 or 200 mg of the active compounds to be tested, were placed in 10 cm high glass beakers which were filled with Kimmig nutrient agar to a height of 5 cm. Before introducing the tampons, holes of the diameter of the tampons were bored in the centre of the agar dishes using sterile cork borers.

The surfaces of the agar in the dishes were then homogeneously inoculated with suspensions of organisms of C. albicans or T. glabrata. The density of organisms was $10^4$ cells per $cm^2$.

The test dishes thus prepared were incubated at 37° C. for 48 hours in an incubation chamber.

In order to obtain a time scale for release of the active compound from the vaginal tampons, of the 2 tampons employed in each case, one was removed from the culture dish after 3 hours and the other after 6 hours.

After the end of the incubation time, the zones of inhibition which had formed round the test holes due to the release of active compound from the tampons were measured.

The sizes of the zones of inhibition for the individual tampon formulations are compiled in the following table.

TABLE

Sizes of zones of inhibition for various vaginal formulations after exposure times of 3 and 6 hours for *C. albicans* and *T. glabrata*.

| Formulation Examples | Size of zone of inhibition in mm ∅ after an exposure time of 3 and 6 hours for | | | |
|---|---|---|---|---|
| | *Candida albicans* | | *Torulopsis glabrata* | |
| | 3 hours | 6 hours | 3 hours | 6 hours |
| 1 | 32 | 32 | 27 | 29 |
| 2 | 37 | 37 | neg. | trace |
| 3 | 40 | 41 | 34 | 35 |
| 4 | 36 | 36 | 30 | 34 |
| 5 | 43 | 44 | 29 | 33 |
| 6 | 37 | 38 | 29 | 31 |
| 7 | 30 | 35 | trace | 25 |
| 8 | 32 | 33 | trace | 26 |
| 9 | 43 | 43 | 29 | 33 |
| 10 | 45 | 45 | 30 | 34 |
| 11 | 40 | 45 | 32 | 35 |
| 12 | 30 | 39 | 24 | 27 |
| 13 | 39 | 40 | 25 | 25 |
| 14 | 35 | 35 | 29 | 31 |
| 15 | 40 | 40 | 38 | 41 |
| 16 | 39 | 39 | 35 | 37 |
| 17 | 40 | 41 | 33 | 35 |
| 18 | 40 | 40 | 32 | 35 |
| 19 | 35 | 36 | 27 | 28 |
| 20 | 39 | 39 | 30 | 29 |
| 21 | 39 | 39 | 37 | 38 |
| 23 | 33 | 34 | 28 | 29 |
| 24 | 34 | 39 | 28 | 28 |
| 25 | 33 | 34 | trace | trace |
| 26 | 32 | 36 | 30 | 30 |
| 27 | 38 | 40 | trace | 30 |
| 28 | 34 | 35 | 26 | 27 |
| 29 | 33 | 36 | 28 | 32 |
| 30 | 34 | 34 | 29 | 30 |
| 31 | 32 | 33 | 27 | 28 |
| 32 | 31 | 32 | 28 | 28 |
| 33 | 30 | 33 | trace | trace |
| 34 | 32 | 37 | neg. | trace |
| 35 | 33 | 39 | 29 | 32 |
| 36 | 34 | 43 | trace | trace |
| 37 | 32 | 40 | neg. | neg. |
| Known tampons [see Curr on Therapeutic Research, Vo. 23, No. 6, June 1978, 661–665] | 30 | 34 | unclear zones of inhibition, growing together | |

What is claimed is:

1. A process for the production of vaginal tampons containing pharmaceutical active compounds, comprising preparing a basic material containing active material and formulation auxiliaries by melting the active compound and the formulation auxiliaries and then cooling the resulting melt to 40° C., injecting said basic material into pre-warmed tampons, which are still wrapped in protective foil from the point by means of a pre-warmed injection syringe, and placing the tampons thus impregnated with a point at the bottom in pre-warmed vessels and thus cooling down slowly.

* * * * *